(12) United States Patent
Zhao

(10) Patent No.: US 9,375,728 B2
(45) Date of Patent: Jun. 28, 2016

(54) AIR FILTER DEVICE HAVING A HIGH-VOLTAGE POWER TRANSMISSION WIRE COLUMN

(76) Inventor: Bing Zhao, Shenzhen (CN)

(*) Notice: Subject to any disclaimer, the term of this patent is extended or adjusted under 35 U.S.C. 154(b) by 167 days.

(21) Appl. No.: 14/366,674

(22) PCT Filed: Jul. 3, 2012

(86) PCT No.: PCT/CN2012/078137
§ 371 (c)(1),
(2), (4) Date: Jun. 18, 2014

(87) PCT Pub. No.: WO2014/005294
PCT Pub. Date: Jan. 9, 2014

(65) Prior Publication Data
US 2014/0366735 A1    Dec. 18, 2014

(51) Int. Cl.
*B03C 3/011* (2006.01)
*A61L 9/22* (2006.01)
*B01D 46/10* (2006.01)
*B01D 46/52* (2006.01)

(52) U.S. Cl.
CPC . *B03C 3/011* (2013.01); *A61L 9/22* (2013.01); *B01D 46/10* (2013.01); *B01D 46/521* (2013.01)

(58) Field of Classification Search
CPC combination set(s) only.
See application file for complete search history.

(56) References Cited

U.S. PATENT DOCUMENTS

| 3,967,131 | A | * | 6/1976 | Slipiec | C01B 13/11 422/186.18 |
| 4,435,190 | A | * | 3/1984 | Taillet | B03C 3/12 239/3 |
| 5,296,019 | A | * | 3/1994 | Oakley | B03C 3/41 361/226 |
| 5,330,559 | A | * | 7/1994 | Cheney | B03C 3/155 95/63 |
| 5,474,600 | A | * | 12/1995 | Volodina | A61L 9/22 96/223 |
| 8,673,068 | B2 | * | 3/2014 | Volodin | A61L 9/22 55/DIG. 38 |
| 8,974,735 | B2 | * | 3/2015 | Morito | A61L 9/205 422/120 |
| 2012/0121470 | A1 | * | 5/2012 | Morito | A61L 9/205 422/121 |

* cited by examiner

*Primary Examiner* — Duane Smith
*Assistant Examiner* — Sonji Turner

(57) ABSTRACT

Disclosed is an air filter device having a high-voltage power transmission wire column. The device comprises: a filter paper, a filter frame, a net base, an ion filament arranged below the filter paper, and a discharge net arranged below the ion filament; the ion filament being installed on an ion filament component, the ion filament component being made of a net-shaped insulation material and being fixed onto the net base; the filter paper being fixed onto the filter frame, and the filter frame being cooperatively connected to the net base; wherein: the discharge net is provided with a ceramic insulating column, a top portion of the ceramic insulating column is connected to the ion filament component, the ceramic insulation column has a hollow through cavity, and a high-voltage connection wire of the ion filament passes through the cavity of the ceramic insulating column.

6 Claims, 2 Drawing Sheets

US 9,375,728 B2

AIR FILTER DEVICE HAVING A HIGH-VOLTAGE POWER TRANSMISSION WIRE COLUMN

TECHNICAL FIELD

The present invention relates to an air purification field, and in particular, to relates to an air filter device.

BACKGROUND

As air pollution is on the rise, an air purification device is preventing more and more importance in aspects of life, medical treatment, and production. Some popular air purification devices on the current market implement purification by using a high-voltage electric field under cooperation with an air filter. Normally, a high-voltage filament and a discharge net are spacingly fixed onto an outer frame, such that the high-voltage filament is not contact with the discharge net. The discharge net is subject to induction through a high voltage to produce an electric field and to implement a biocidal treatment. The outer frame is normally made of fire barrier plastic, but during use, such impurities as dust are easily absorbed onto a fixed point of the high-voltage filament on the outer frame the device operates under a high voltage; after long time use, the impurities such as dust are carbonized, and the plastic on the fixed point portion is carbonized; the carbonized plastic is easily fired, which brings potential safety hazards.

SUMMARY OF THE INVENTION

The present invention provides an air filter device having a discharge net column, to solve the problem that plastic components carbonized due to electric shock caused by a high voltage in the prior art.

An air filter device having a high-voltage power transmission wire column is provided, comprising: a filter paper, a filter frame, a net base, an ion filament arranged below the filter paper, and a discharge net arranged below the ion filament; the ion filament being installed on an ion filament component, the ion filament component being made of a net-shaped insulation material and being fixed onto the net base; the filter paper being fixed onto the filter frame, and the filter frame being cooperatively connected to the net base; wherein: the discharge net is provided with a ceramic insulating column, a top portion of the ceramic insulating column is connected to the ion filament components, the ceramic insulation column has a hollow through cavity, and a high-voltage connection wire of the ion filament passes through the cavity of the ceramic insulating column.

Preferably, an upper portion of the ceramic insulating column is provided with a fire barrier sealing plug, and the high-voltage connection line passes through the filer barrier sealing plug and enters the cavity of the ceramic insulating column.

Preferably, a top surface of an air duct is arranged below the discharge net, and the discharge net is fixed onto the top surface of the air duct through a support column.

Preferably, a lower portion of the net base is fixed onto an upper surface of the top surface of the air duct.

Preferably, the discharge net is further provided with two ceramic columns which are evenly distributed with the ceramic insulating column on an upper surface of the discharge net.

Preferably, a lower surface of the ion filament component is provided with a groove capable of accommodating a peak portion of the ceramic column, and the peak portion of the ceramic column mates with the groove.

According to the above technical solution, when the device according to the present invention operates, the ion filament is input with high voltage through a high-voltage connection wire, and inducts with the discharge net to produce an electric field. But the ion filament absorbs numerous dust and impurity at the same time, such that the dust and impurity are deposited on the ceramic insulating column. After long time use, the dust and impurity deposited on the surface of the ceramic insulating column are carbonized due to electric shock caused by the high voltage. The material body of the ceramic insulating column has the feature of high temperature resistance and is not affected by the carbonized dust and impurity, and therefore potential safety hazards are simply prevented. Meanwhile, the high-voltage connection wire passes through the cavity of the ceramic insulating column, and is connected to the ion filament. The ceramic insulating column protects the high-voltage connection wire, thereby preventing production of the electric field during the usage of the ion filament, and preventing the high-voltage connection line from absorbing dust and impurity which may bring damages and hazards to the high-voltage connection wire.

According to the present invention, a periphery of the discharge is not in contact with the net base, but is only connected to the underside of the ion filament component through the ceramic insulating column, thereby preventing ignition of high voltage and improving safety during use of the device.

DESCRIPTION OF EMBODIMENTS

To make the objective, technical solution, and advantages of the present invention clearer, the present invention is further described with reference to specific embodiments and attached drawings. It should be understood that the embodiments described herein are only for illustrating the present invention, but are not intended to limit the present invention.

Figure 1:
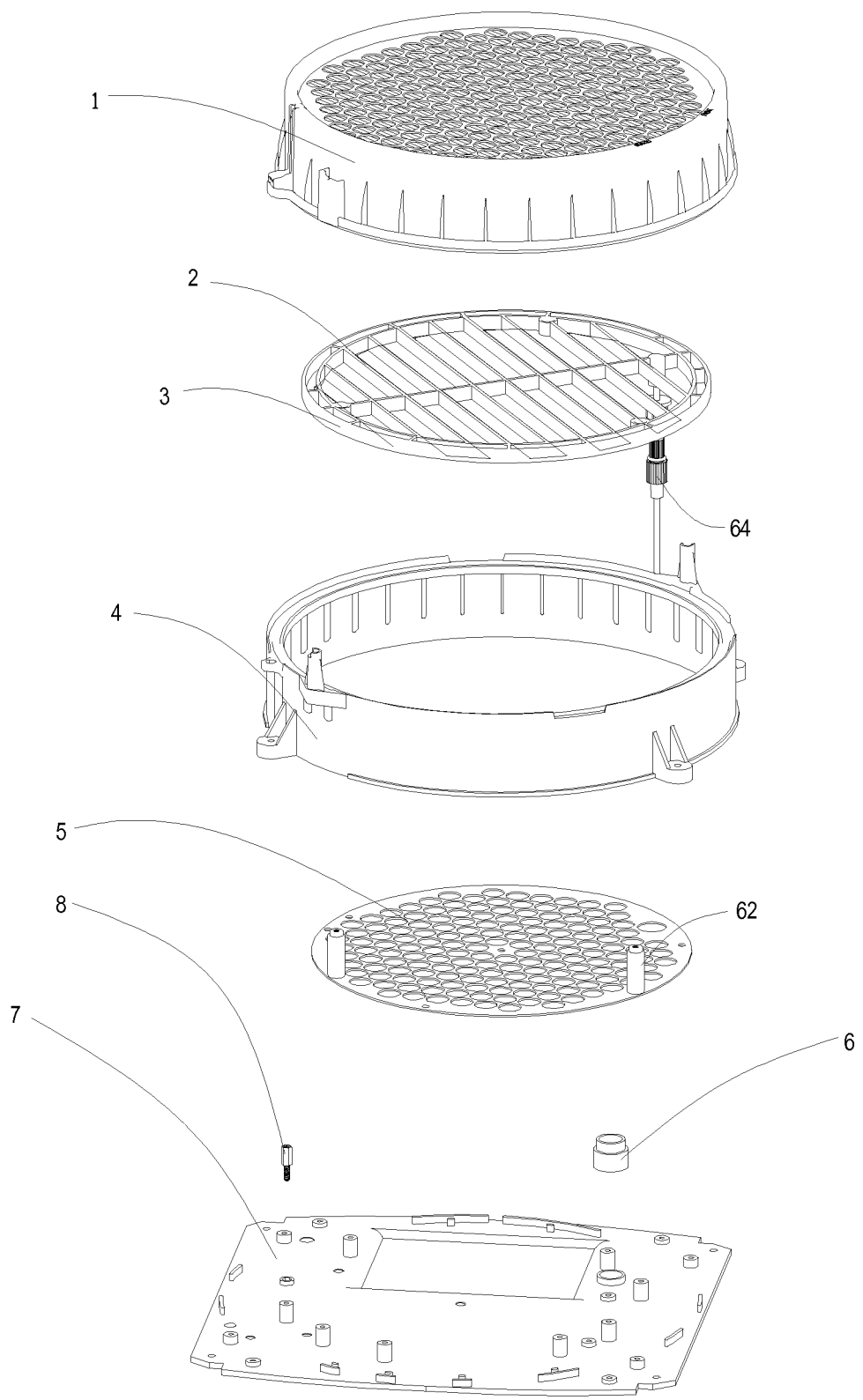
FIG. 1 is a schematic exploded view of a product according to an embodiment of the present invention.
Figure 2:
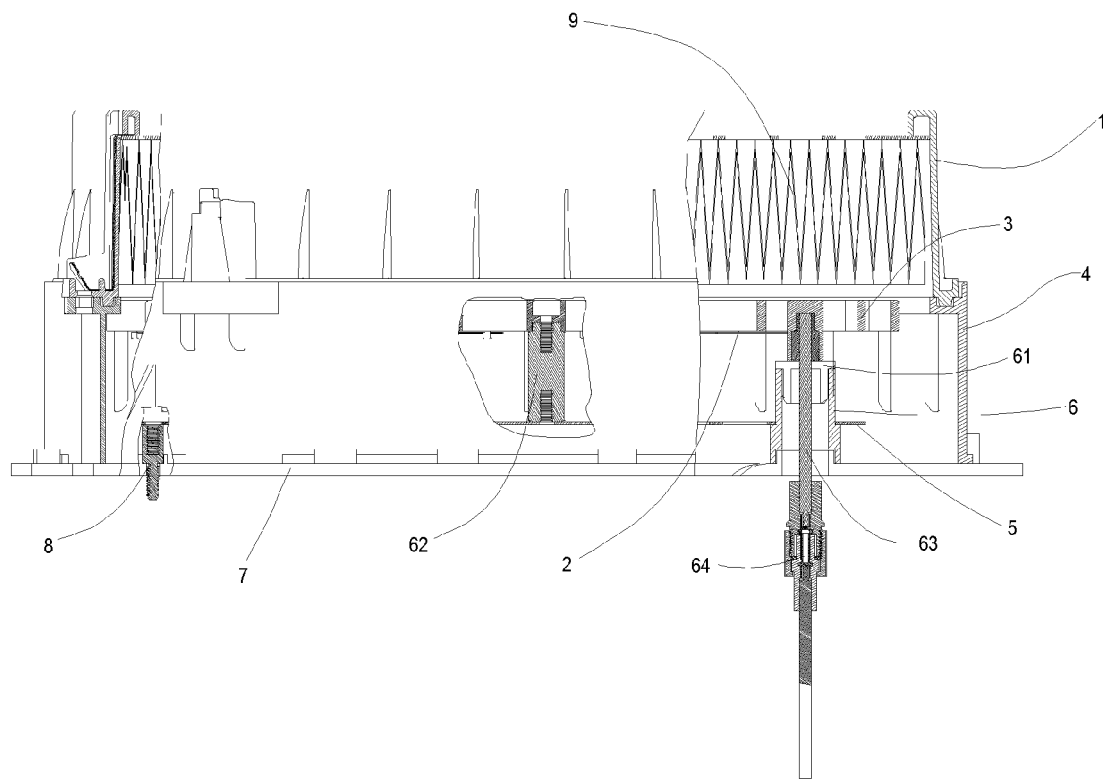
FIG. 2 is a partial section view of the product taken from a side of the product according to the embodiment of the present invention.

Referring to FIG. 1 and FIG. 2, this invention provides an air filter device having a high-voltage power transmission wire column, comprising: a filter paper 9, a filter frame 1, a net base 4, an ion filament 2 arranged below the filter paper 9, and a discharge net 5 arranged below the ion filament 2; the ion filament 2 being installed on an ion filament component 3, the ion filament component 3 being made of a net-shaped insulation material and being fixed onto the net base 4; the filter paper 9 being fixed onto the filter frame 1, and the filter frame 1 being cooperatively connected to the net base 4; wherein: the discharge net 5 is provided with a ceramic insulating column 6, a peak portion of the ceramic insulating column 6 is connected to the ion filament component 3, the ceramic insulation column 6 has a hollow through cavity, and a high-voltage connection wire 63 of the ion filament 2 passes through the cavity of the ceramic insulating column 6. According to the above technical solution, when the device according to the present invention operates, the ion filament 2 is input with high voltage through a high-voltage connection wire 63 connected with a high voltage output terminal 64, and inducts with the discharge net 5 to produce an electric field.

But the ion filament 2 absorbs numerous dust and impurity at the same time, such that the dust and the impurity are deposited on the ceramic insulating column 6. After long time use, the dust and the impurity deposited on the surface of the ceramic insulating column 6 are carbonized due to the electric shock caused by the high voltage. The material body of the ceramic insulating column 6 has the feature of high temperature resistance and is not affected by the carbonized dust and impurity, and therefore potential safety hazards are simply prevented. Meanwhile, the high-voltage connection wire 63 passes through the cavity of the ceramic insulating column 6, and is connected to the ion filament 2. The ceramic insulating column 6 protects the high-voltage connection wire 63, thereby preventing production of an electric field during the usage of the ion filament 2, and preventing the high-voltage connection wire 63 from absorbing dust and impurity which may bring damages and hazards to the high-voltage connection wire 63. In the present invention, a periphery of the discharge net 5 is not in contact with the net base 4, but is only connected to the underside of the ion filament component 3 through the ceramic insulating column 6, thereby preventing ignition of high voltage and improving safety during use of the device.

For further sealing the high-voltage connection wire 63 in an inner cavity of the ceramic insulating column 6, an upper portion of the ceramic insulating column 6 is provided with a fire barrier sealing plug 61, and the high-voltage connection wire 63 passes through the fire barrier sealing plug 61 and enters the cavity of the ceramic insulating column 6. A lower portion of the ceramic insulating column 6 is connected to the discharge net 5, and the high-voltage connection wire 63 passes through an opening of the discharge net 5. In this way, a circuit is lead out.

A top surface 7 of an air duct is arranged below the discharge net 5, and the discharge net 5 is fixed onto the top surface 7 of the air duct through a support column 8. The top surface 7 of the air duct is positioned in a fan outlet of an air purification and filter device, and is made of an insulation material to support the discharge net 5, thereby preventing the discharge net 5 from contacting the net base 4. The lower portion of the net base 4 is fixed onto an upper surface of the top surface 7 of the air duct. Because the net base 4 is also made of an insulation material, the area of the net base 4 is bigger than the area of the discharge net 5, and a periphery of the discharge net 5 is not in contact with the net base 4, thereby preventing dust and impurity from being deposited in a partial area of the net base 4 when the electric field is produced by the high voltage power carried on the ion filament 2 under cooperation with the discharge net 5. Further, for better fixing of ion filament component 3, the discharge net 5 is further provided with two ceramic columns 62 which are evenly distributed with the ceramic insulating column 6 on an upper surface of the discharge net 5. For convenient fixing of the ion filament component 3 on the ceramic columns 62, a lower surface of the ion filament component 3 is provided with a groove capable of accommodating a peak portion of the ceramic column 62, and the peak portion of the ceramic column 62 mates with the groove.

Detailed above are merely preferred embodiments of the present invention, but are not intended to limit the present invention. Any modification, equivalent replacement, or improvement made without departing from the spirit and principle of the present invention should fall within the protection scope of the present invention.

What is claimed is:

1. An air filter device having a high-voltage power transmission wire column, comprising: a filter paper, a filter frame, a net base, an ion filament arranged below the filter paper, and a discharge net arranged below the ion filament; the ion filament being installed on an ion filament component, the ion filament component being made of a net-shaped insulation material and being fixed onto the net base; the filter paper being fixed onto the filter frame, and the filter frame being cooperatively connected to the net base; wherein: the discharge net is provided with a ceramic insulating column, a top portion of the ceramic insulating column is connected to the ion filament component, the ceramic insulation column has a hollow through cavity, and a high-voltage connection wire of the ion filament passes through a cavity of the ceramic insulating column.

2. The air filter device according to claim 1, wherein an upper portion of the ceramic insulating column is provided with a fire barrier sealing plug, and the high-voltage connection wire passes through the fire barrier sealing plug and enters the cavity of the ceramic insulating column.

3. The air filter device according to claim 2, wherein a top surface of an air duct is arranged below the discharge net, and the discharge net is fixed onto the top surface of the air duct through a support column.

4. The air filter device according to claim 3, wherein a lower portion of the net base is fixed onto an upper surface of the top surface of the air duct.

5. The air filter device according to claim 4, wherein the discharge net is further provided with two ceramic columns which are evenly distributed with the ceramic insulating column on an upper surface of the discharge net.

6. The air filter device according to claim 5, wherein a lower surface of the ion filament component is provided with a groove capable of accommodating a peak portion of the ceramic column, and the peak portion of the ceramic column mates with the groove.

* * * * *